(12) United States Patent
Xue et al.

(10) Patent No.: US 7,840,259 B2
(45) Date of Patent: Nov. 23, 2010

(54) METHOD AND SYSTEM FOR ELECTROCARDIOGRAM EVALUATION

(75) Inventors: Joel Qiuzhen Xue, Germantown, WI (US); Johannes Jan Struijk, Aalborg Øst (DK); Mads Peter Andersen, Aalborg Ø (DK); Claus Graff, Klarup (DK); Thomas Bork Hardahl, Aalborg (DK)

(73) Assignee: General Electric Company, Schenectady, NY (US)

( * ) Notice: Subject to any disclaimer, the term of this patent is extended or adjusted under 35 U.S.C. 154(b) by 492 days.

(21) Appl. No.: 11/622,046

(22) Filed: Jan. 11, 2007

(65) Prior Publication Data

US 2008/0154143 A1      Jun. 26, 2008

Related U.S. Application Data

(60) Provisional application No. 60/871,495, filed on Dec. 22, 2006.

(30) Foreign Application Priority Data

Nov. 30, 2006   (DK)   ................. 2006 01579

(51) Int. Cl.
   *A61B 5/04*   (2006.01)
(52) U.S. Cl. ..................................... 600/509
(58) Field of Classification Search ......... 600/508–525; 342/377, 381, 285, 296, 348; 375/285, 296, 375/348; 382/228; 368/10
See application file for complete search history.

(56) References Cited

U.S. PATENT DOCUMENTS

| 5,634,469 | A | * | 6/1997 | Bruder et al. | ................ 600/512 |
| 5,711,304 | A | * | 1/1998 | Dower | ........................ 600/523 |
| 5,713,367 | A | * | 2/1998 | Arnold et al. | ................ 600/517 |
| 5,792,065 | A | * | 8/1998 | Xue et al. | .................... 600/516 |
| 6,358,214 | B1 | * | 3/2002 | Tereschouk | ................. 600/508 |
| 6,389,308 | B1 | * | 5/2002 | Shusterman | ................ 600/509 |

(Continued)

FOREIGN PATENT DOCUMENTS

WO    WO2005058156    6/2005

(Continued)

OTHER PUBLICATIONS

John G. Webster, Editor. "Biopotential Amplifiers" by Michael R. Neuman, Medical Instrumentation—Application and Design. 1998, p. 235-241. Third Edition, John Wiley & Sons, Inc, New York.

(Continued)

*Primary Examiner*—George Manuel
*Assistant Examiner*—Robert N Wieland
(74) *Attorney, Agent, or Firm*—Andrus, Sceales, Starke & Sawall, LLP

(57) ABSTRACT

A method for evaluating an electrocardiogram is disclosed herein. The method includes measuring an electrical activity of a patient, processing the measured electrical activity to form a multi-lead signal, and extracting a segment of the multi-lead signal. The method for evaluating an electrocardiogram also includes transforming the segment of the multi-lead signal into a synthesized signal that is most representative of the patient's electrical activity, and evaluating the synthesized signal. A corresponding system for evaluating an electrocardiogram is also disclosed.

14 Claims, 3 Drawing Sheets

U.S. PATENT DOCUMENTS

| | | | |
|---|---|---|---|
| 6,438,409 B1 * | 8/2002 | Malik et al. | 600/512 |
| 7,072,709 B2 | 7/2006 | Xue | |
| 7,142,907 B2 | 11/2006 | Xue et al. | |
| 7,266,048 B1 * | 9/2007 | King et al. | 368/10 |
| 2004/0002661 A1 * | 1/2004 | Schreck | 600/509 |
| 2004/0162495 A1 | 8/2004 | Quenet et al. | |
| 2005/0038352 A1 * | 2/2005 | Xue et al. | 600/523 |
| 2005/0209525 A1 * | 9/2005 | Bojovic et al. | 600/512 |

FOREIGN PATENT DOCUMENTS

| | | |
|---|---|---|
| WO | 2008064682 | 6/2008 |

OTHER PUBLICATIONS

Zabel Markus et al: "Analysis of T-wave Morphology from the 12-lead Electrocardiogram for Prediction of Long-term Prognosis in Male US Veterans." Circulation, vol. 105, No. 9, Mar. 5, 2002, pp. 1066-1070.

Ng J et al: "Vector Analysis of Atrial Activity from Surface ECGs Recorded During Atrial Fibrillation" Computers in Cardiology 2002, vol. 29, Sep. 22, 2002, pp. 21-24.

Malik Marek: "Assessment of T-wave Morphology." Mayo Clinic Proceedings 2003, vol. 78, pp. 18-20.

Couderc J P et al: "Electrocardiographic Method for Identifying Drug-Induced Repolarization Abnormalities Associated with a Reduction of the Rapidly Activating Delayed Rectifier Potassium Current" Conf Proc EMBS 2006 28th Annual International Conference of the IEEE, Aug. 30-Sep. 3, 2006, vol. 1, pp. 4010-4015.

* cited by examiner

METHOD AND SYSTEM FOR ELECTROCARDIOGRAM EVALUATION

CROSS REFERENCE TO RELATED APPLICATIONS

The present application claims priority from provisional application Ser. No. 60/871,495, filed Dec. 22, 2006.

FIELD OF THE INVENTION

This invention pertains generally to a system and method for the evaluation of an electrocardiogram.

BACKGROUND OF THE INVENTION

An electrocardiogram (ECG) of a single heartbeat is commonly referred to as a PQRST complex. The PQRST wave includes a P-wave that corresponds to activity in the atria, a QRS complex that represents the electrical activation of the ventricles, and a T-wave that represents the electrical recovery or recharge phase of the ventricles. The QT interval is the time between the QRS onset and the end of the T-wave, and is commonly measured for purposes of evaluating cardiac electrical stability and thereby predicting potentially life threatening medical conditions such as cardiac arrhythmia. Some pharmaceuticals have side affects that increase the QT interval of an otherwise healthy patient and induce unstable cardiac electrical activity. Therefore, the FDA has begun to perform a drug-induced QT study on new pharmaceuticals prior to their approval. One problem is that an increase in QT interval is not directly correlated with cardiac electrical instability and another problem is that the QT interval is difficult to precisely measure. Therefore, if we only rely on the QT interval, there is the potential for the exclusion of beneficial pharmaceuticals based on the erroneous assumption that they may cause electrical instability and malignant cardiac arrhythmias.

Studies have shown that an increase of heterogeneity in the re-polarization of the heart is directly linked to cardiac electrical instability. Accordingly, an attempt has been made to find the ECG features which have a higher correlation with the heterogeneity of the re-polarization as an indicator of cardiac electrical instability. More recently, it has been determined that the shape of the T-wave is an ECG feature that can be evaluated to more accurately asses cardiac electrical stability. As an example, T-wave flatness, asymmetry, and the presence of a "notch" in the T-wave have been correlated with unstable cardiac electrical activity. The problem is that, although T-wave shape observation has the potential to more accurately assess cardiac electrical stability, its consistency relies on the quality of data defining the T-wave. For example, a twelve lead ECG provides 12 separate T-waves representing different electrical views/projections of cardiac re-polarization. Therefore, if the optimal and most consistent T-wave representation is not implemented for observation, it will be difficult to assess a re-polarization abnormality based on any particular lead.

Another problem relates to the placement of the sensors or transducers on a patient for the purpose of monitoring the electrical activity of the patient's heart. The conventional process involves placing multiple sensors at a variety of locations selected to optimally monitor the electrical activity. As the optimal sensor placement location varies during the course of the electrical cycle, and varies from patient to patient, it is currently not feasible to ensure that a sensor is placed at every optimal location for every patient.

SUMMARY OF THE INVENTION

The above-mentioned shortcomings, disadvantages and problems are addressed herein which will be understood by reading and understanding the following specification.

In an embodiment, a method for evaluating an electrocardiogram includes measuring an electrical activity of a patient, processing the measured electrical activity to form a multi-lead signal, and extracting a segment of the multi-lead signal. The method for evaluating an electrocardiogram also includes transforming the segment of the multi-lead signal into a synthesized signal that is most representative of the patient's electrical activity, and evaluating the synthesized signal.

In another embodiment, a method for evaluating an electrocardiogram includes measuring an electrical activity of a patient, processing the measured electrical activity to form a multi-lead signal, converting the multi-lead signal into a multi-dimensional representation, and extracting a segment from the multi-dimensional representation. The method for evaluating an electrocardiogram also includes performing a principal component analysis on the multi-dimensional representation to provide a synthesized signal that is most representative of the patient's electrical activity, and evaluating the synthesized signal.

In yet another embodiment, a system for evaluating an electrocardiogram includes a plurality of leads attachable to a patient. The plurality of leads are configured to measure an electrical activity of the patient. The system for evaluating an electrocardiogram also includes a diagnostic system operatively connected to the plurality of leads. The diagnostic system is configured to form a multi-lead signal based on the measured electrical activity, extract a segment of the multi-lead signal, and transform the segment of the multi-lead signal into a synthesized signal that most accurately reflects the patient's electrical activity.

Various other features, objects, and advantages of the invention will be made apparent to those skilled in the art from the accompanying drawings and detailed description thereof.

DETAILED DESCRIPTION OF THE INVENTION

In the following detailed description, reference is made to the accompanying drawings that form a part hereof, and in which is shown by way of illustration specific embodiments that may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken as limiting the scope of the invention.

Figure 1:
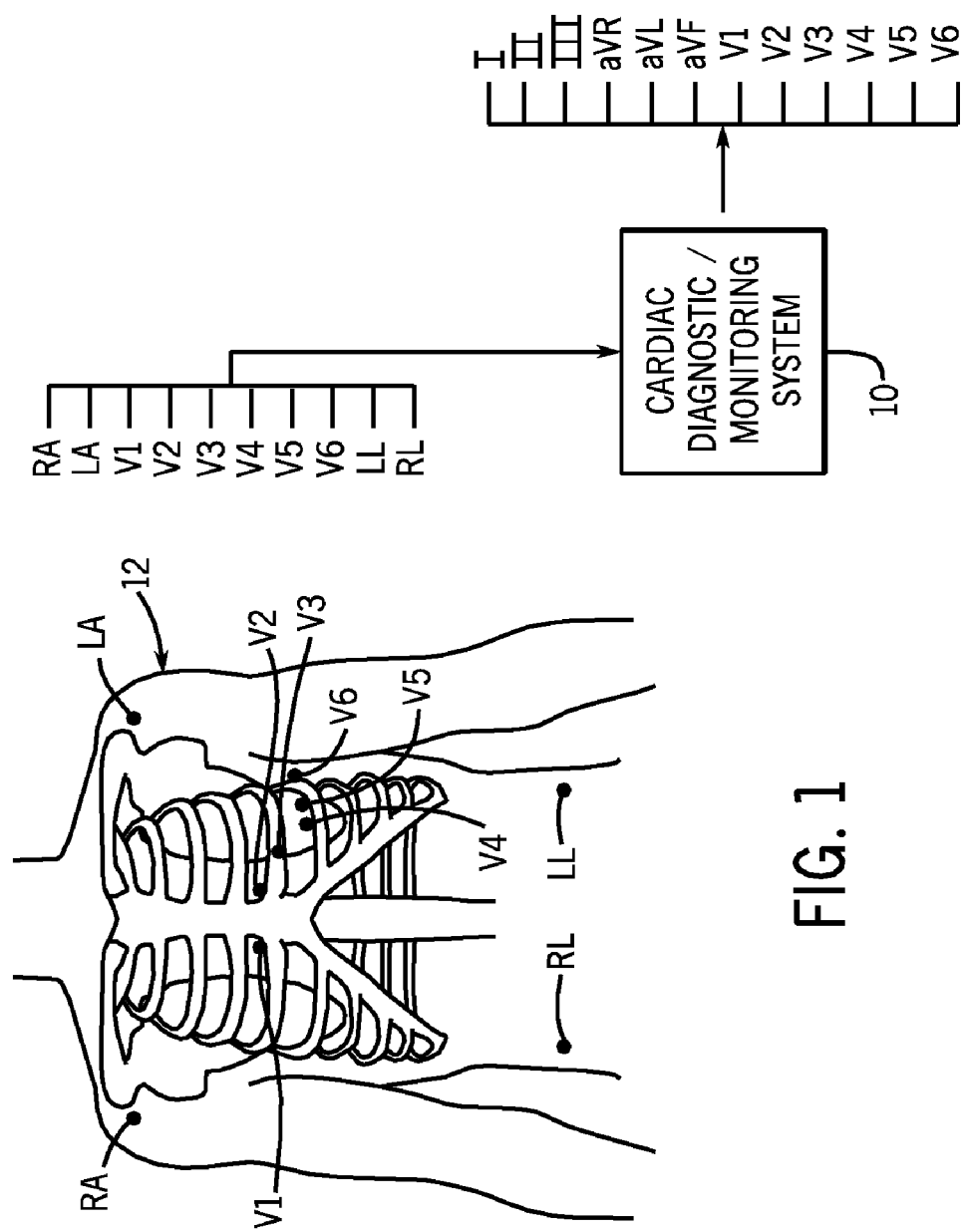
FIG. 1 is a schematic illustration of a cardiac diagnostic/monitoring system operatively connected to a patient via a twelve lead system in accordance with an embodiment.

Referring to FIG. 1, a schematically represented cardiac diagnostic/monitoring system 10 is adapted measure an electrical signal generated by a patient's heart. The cardiac diagnostic/monitoring system 10 can be coupled to the patient 12 by an array of sensors or transducers. In the illustrated embodiment, the array of sensors include a right arm electrode RA; a left arm electrode LA; chest electrodes V1, V2, V3, V4, V5 and V6; a right leg electrode RL; and a left electrode leg LL for acquiring a standard twelve lead, ten-electrode electrocardiogram (ECG) signal. The twelve ECG leads include leads I, II, V1, V2, V3, V4, V5 and V6 which are acquired directly from the patient leads, and leads III, aVR, aVL and aVF which are derived using Einthoven's law. In other embodiments, alternative configurations of sensors and sensor locations can be used to acquire a standard or non-standard ECG signal. For example, an expanded fifteen lead system, including four extra electrodes, can be used to form Frank X, Y and Z leads.

Figure 2:
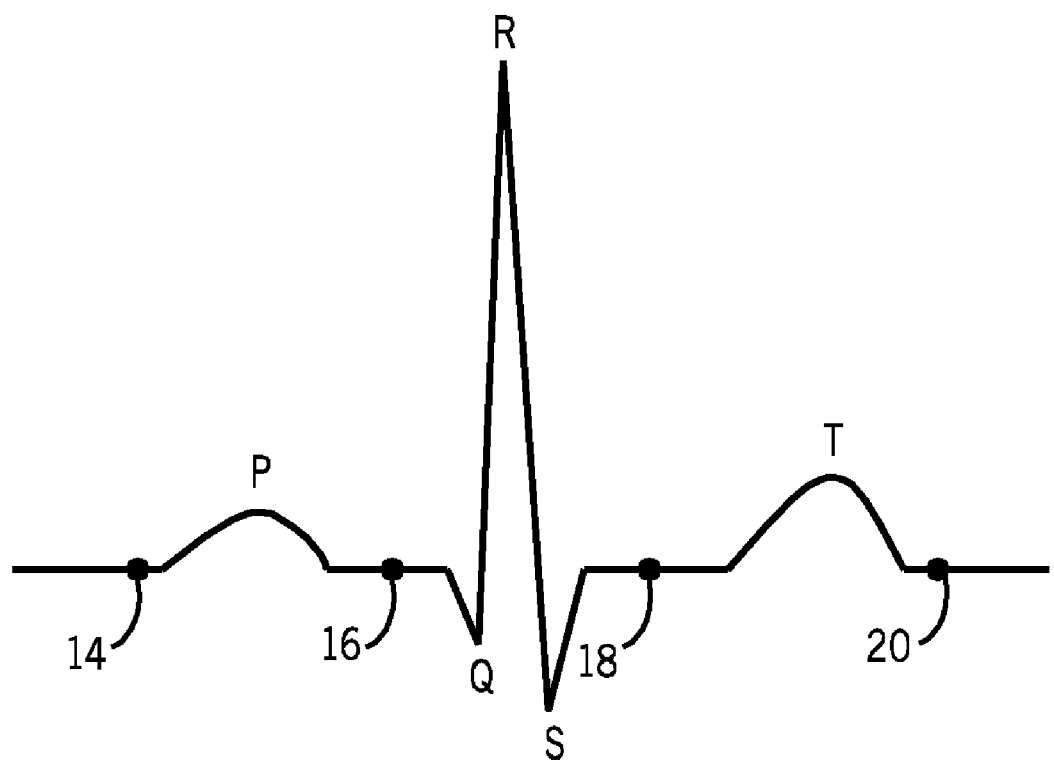
FIG. 2 is an electrocardiogram.

Referring to FIG. 2, an electrocardiogram of a single heartbeat typically referred to as a PQRST complex is shown. The portion of the PQRST complex defined between reference points 14 and 16 is defined as the P-wave, and corresponds to activity in the atria. The portion of the PQRST complex defined between reference points 16 and 18 is defined as the QRS complex, and represents the electrical activation of the ventricles. The portion of the PQRST complex defined between reference points 18 and 20 is defined as the T-wave, and represents the electrical recovery or recharge phase of the ventricles. As is known in the art, the distinct portions or segments of the PQRST complex can be broken up and individually evaluated through a process known as segment extraction. It has been observed that an evaluation of the shape of an extracted T-wave can be used to evaluate the electrical stability of a patient's heart. For example, it is known that overly flat T-waves, certain shapes of asymmetric T-waves, and T-waves that include one or more "notches" are linked to unstable cardiac electrical activity that can lead, for example, to cardiac arrhythmia. T-wave shape evaluation may be performed manually or may be automated such as with a computer algorithm configured to identify T-wave data falling outside a predefined range.

The twelve ECG leads (e.g., leads I, II, III, V1, V2, V3, V4, V5, V6, aVR, aVL and aVF) obtained by the cardiac diagnostic/monitoring system 10 (shown in FIG. 1) produce twelve different electrocardiograms that represent the electrical activity of a patient's heart with varying degrees of precision. The degree of precision with which a particular lead represents the heart's electrical activity is based in part on the placement of the corresponding electrode or electrodes. The electrodes V1, V2, V3, V4, V5, V6, RA, LA, RL, LL that are in closest proximity to and/or are most optimally aligned with the electrical activity of the heart at any given time receive the strongest signal and are therefore best adapted to monitor such electrical activity. Accordingly, the ECG lead based on an electrode or electrodes that are in closest proximity to and/or are most optimally aligned with the electrical activity of the heart generally provide the most accurate reflection of this electrical activity.

The optimal location on a given patient for electrode placement varies during the course of the heart's electrical cycle, and varies from patient to patient. Therefore, it is often the case that variation of the placement of the electrodes V1, V2, V3, V4, V5, V6, RA, LA, RL, LL can affect the diagnostic accuracy. As will be described in detail hereinafter, an embodiment of this invention estimates the data that would be provided from a robust representative lead even if none of the electrodes are accurately placed on the patient 12. Advantageously, this provides the most accurate and reflective data for purposes of generating and evaluating an electrocardiogram.

Having described the cardiac diagnostic/monitoring system 10 in accordance with an embodiment, a method for electrocardiogram evaluation will now be described. The method will hereinafter be described as being applied to the T-wave segment of an electrocardiogram for purposes of evaluating T-wave shape. It should, however, be appreciated that alternative methods may be applied to an entire electrocardiogram, or to any other electrocardiogram segment.

Figure 3:
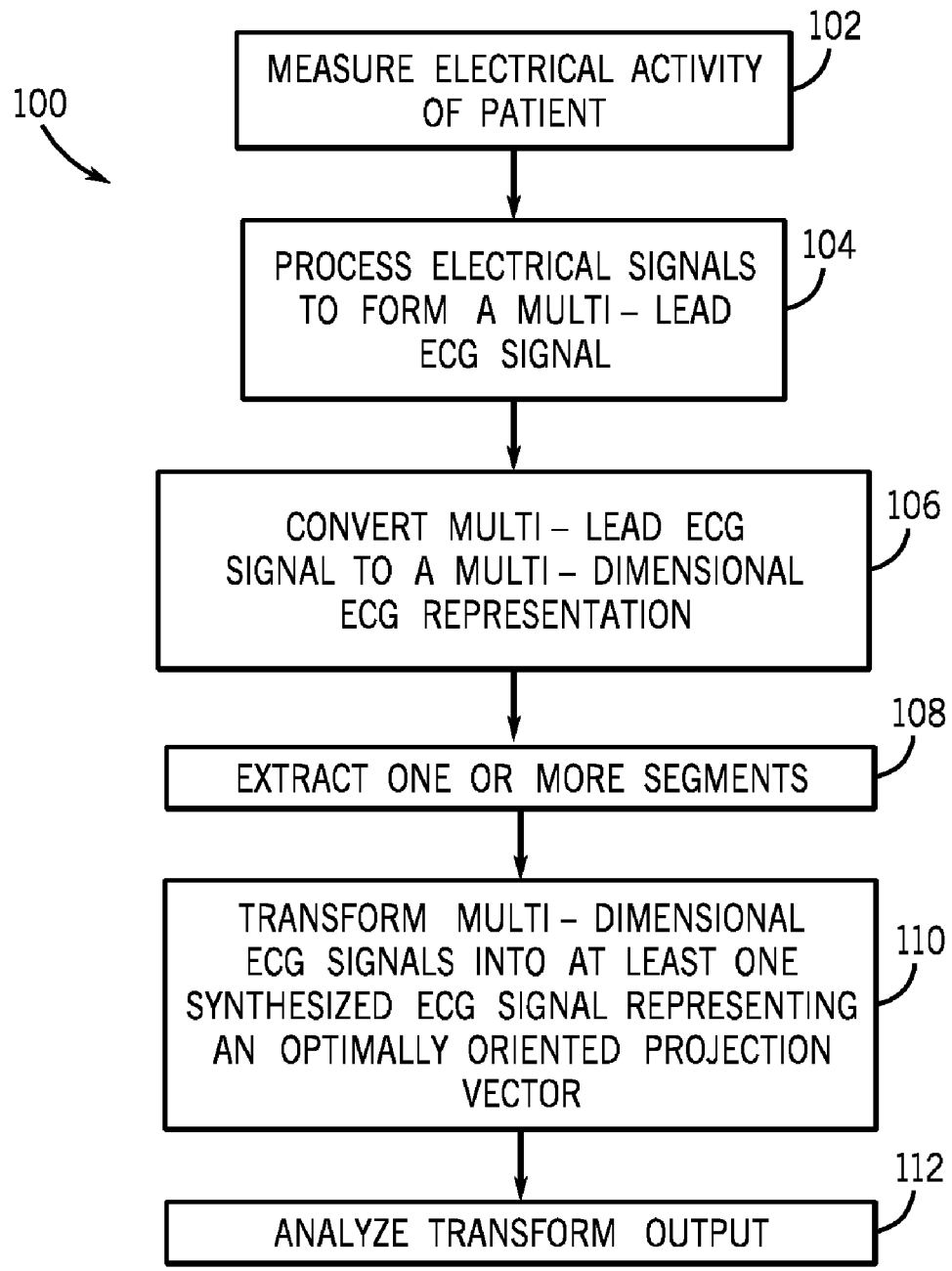
FIG. 3 is a block diagram illustrating a method in accordance with an embodiment.

Referring to FIG. 3, a block diagram illustrates a method 100. The individual blocks 102-112 represent steps that may be performed in accordance with the method 100. Unless otherwise specified, the steps 102-112 need not be performed in the order shown.

At step 102, a patient's electrical activity is measured such as, for example, with the cardiac diagnostic/monitoring system 10 (shown in FIG. 1). According to one example, the electrical activity measured at step 102 is produced by the patient's heart. The patient may be a human or an animal.

At step 104, the electrical activity measured at step 102 is processed to form a multi-lead ECG signal such as, for example, with the cardiac diagnostic/monitoring system 10. According to the exemplary embodiment illustrated in FIG. 1, the multi-lead ECG signal is a twelve lead ECG signal including the leads I, II, III, V1, V2, V3, V4, V5, V6, aVR, aVL and aVF.

Step 106 is an optional step wherein the multi-lead ECG signal of step 104 is converted to a multi-dimensional ECG representation. According to one embodiment, the multi-lead ECG signal is a twelve lead ECG signal, and the multi-dimensional ECG representation is a three-dimensional ECG representation having orthogonal X, Y and Z leads. Step 106 can be skipped if the cardiac diagnostic/monitoring system 10 (shown in FIG. 1) is replaced with a system adapted to provide orthogonal X, Y and Z lead data such as, for example, the Frank lead system. The following equations may be implemented to convert twelve lead data (eight independent leads) into orthogonal X, Y and Z lead data:

$$X=-0.1106*v1+0.045*v2-0.04*v3+0.2146*v4-0.067*v5+0.6868*v6+0.3872*I-0.1993*II$$

$$Y=0.1855*v1-0.0728*v2+0.0186*v3+0.0154*v4-0.1148*v5+0.0682*v6-0.0695*I+1.145*II$$

$$Z=0.3665*v1-0.0363*v2+0.165*v3+0.2041*v4+0.1395*v5-0.4688*v6+0.0587*I+0.0815*II$$

This conversion matrix was developed from 5,000 fifteen lead ECG systems (i.e., standard twelve lead plus Frank X, Y and Z lead systems), and a regression analysis run between 5,000 paired twelve lead and Frank X, Y and Z lead systems. Any other known methods for converting from a multi-lead ECG signal to a multi-dimensional ECG representation, such as the inverse Dower method, may alternatively be implemented at step 106. According to the exemplary embodiment wherein the multi-dimensional ECG representation is a three-dimensional representation, the orthogonal X, Y and Z lead data models the heart as a three-dimensional dipole source producing an electrical signal that varies based on the distance from the heart in the X, Y and Z directions. This is known as a dipole vector model, and the X, Y and Z lead data respectively defines the X, Y and Z components of the dipole source.

Step 108 is an optional step in which one or more segments of the PQRST complex (shown in FIG. 2) are extracted. According to one embodiment, the T-wave segment of the PQRST complex is extracted at step 108. According to another embodiment, both the T-wave and the QRS complex segments of the PQRST complex are extracted.

At step 110, the multi-dimensional ECG signals of step 106 are transformed into at least one synthesized ECG signal representing an optimally oriented projection vector. The synthesized ECG signal defines the highest energy vector at any given time. The "highest energy vector" conveys both magnitude and direction of the cardiac electrical activity as measured by an optimally placed electrode. Even if none of the electrodes V1, V2, V3, V4, V5, V6, RA, LA, RL, LL (shown in FIG. 1) are actually placed in the optimal location, the synthesized ECG signal still provides an estimate of the data that would represent the major heart re-polarization activity. The synthesized ECG signal of step 110 yields a more robust representation of heart's actual electrical activity than would otherwise be obtainable by selecting a single physically obtained or derived lead. According to one embodiment, the transform of step 110 is obtained by performing principal component analysis (PCA) on the multi-dimensional ECG signals of step 106. Principal component analysis is known to those skilled in the art and therefore will not be described in detail. According to alternate embodiments, the transform of step 110 may be performed by other processes such as independent component analysis (ICA), nonlinear component analysis (NLCA), factor analysis (FA), projection pursuit (PP), singular value decomposition (SVD), and similar techniques.

At step 112, the output of the transform performed at step 110 is analyzed. It should be appreciated that many different types of analyses can benefit from the method 100 as the data on which the analysis is based is most reflective of the patient's actual electrical cardiac activity. In a non-limiting manner, the following will describe several exemplary analyses that may be performed at step 112.

According to an embodiment wherein the T-wave segment of the PQRST complex is extracted at step 108, the analysis of step 112 may include evaluating the shape of the T-wave defined by a principal PCA vector. The T-wave shape evaluation may look for features such as flatness, asymmetry, and the presence of a notch which are linked to unstable cardiac electrical activity.

According to an embodiment wherein the T-wave segment of the PQRST complex is extracted at step 108, the analysis of step 112 may include evaluating the shape of the T-wave defined by a second PCA vector. The T-wave shape evaluation may look for features such as flatness, asymmetry, and the presence of a notch which are linked to unstable cardiac electrical activity.

According to an embodiment wherein the T-wave segment of the PQRST complex is extracted at step 108, the analysis of step 112 may include evaluating the orientation of the principal PCA vector relative to the second PCA vector.

According to an embodiment wherein the T-wave segment of the PQRST complex is extracted at step 108, the analysis of step 112 may include evaluating the orientation of the projection vector represented by the synthesized ECG signal relative to the X, Y and Z lead vectors. These angles can be calculated using basic geometry principles as will be appreciated by those skilled in the art. The orientation of the projection vector represented by the synthesized ECG signal relative to the X, Y and Z lead vectors is one of the features that is indicative of cardiac electrical stability such that the method 100 can be used to predict heart problems including arrhythmia.

According to an embodiment wherein both the T-wave and the QRS complex segments of the PQRST complex are extracted at step 108, the analysis of step 112 may include evaluating the orientation of the projection vector representing the T-wave relative to the projection vector representing the QRS complex. The orientation of the projection vector representing the T-wave relative to the projection vector representing the QRS complex is indicative of cardiac electrical stability such that the method 100 can be used to predict heart problems including arrhythmia.

According to an embodiment wherein both the T-wave and the QRS complex segments of the PQRST complex are extracted at step 108, the analysis of step 112 may include evaluating the length of the QT interval as represented by the synthesized ECG signal. The length of the QT interval is indicative of cardiac electrical stability and therefore can be used to predict heart problems including arrhythmia.

While the invention has been described with reference to preferred embodiments, those skilled in the art will appreciate that certain substitutions, alterations and omissions may be made to the embodiments without departing from the spirit of the invention. Accordingly, the foregoing description is meant to be exemplary only, and should not limit the scope of the invention as set forth in the following claims.

We claim:

1. A method for evaluating an electrocardiogram (ECG) comprising:

measuring an electrical activity of a complete heartbeat of a patient using a cardiac monitoring system;

processing the measured electrical activity in the cardiac monitoring system to form a twelve lead ECG signal for the complete heartbeat;

obtaining a multi-dimensional ECG representation for the complete heartbeat having orthogonal X, Y and Z lead data from the twelve lead signal;

extracting a segment of the complete heartbeat from the orthogonal X, Y and Z lead data;

transforming the segment of the orthogonal X, Y and Z lead data into a synthesized signal that is most representative of the patient's electrical activity during the extracted segment; and evaluating the orientation of a projection vector for the extracted segment defined by the synthesized signal.

2. The method of claim 1, wherein said transforming the orthogonal X, Y and Z lead data includes performing a principal component analysis on the orthogonal X, Y and Z lead data.

3. The method of claim 1, wherein said extracting a segment includes extracting a T-wave segment, and wherein said evaluating the synthesized signal includes evaluating the shape of the T-wave segment defined by the synthesized signal.

4. The method of claim 1, wherein said extracting a segment includes extracting a T-wave segment.

5. The method of claim 4, wherein said evaluating the orientation of a projection vector includes evaluating the orientation of a projection vector with respect to a physical orientation of the patient.

6. The method of claim 1, wherein said extracting a segment includes extracting a T-wave segment and a QRS complex segment, and wherein said evaluating the synthesized signal includes evaluating the length of the QT interval as defined by the synthesized signal.

7. A method for evaluating an electrocardiogram (ECG) comprising:

measuring an electrical activity of a complete heartbeat of a patient using a cardiac monitoring system;

processing the measured electrical activity in the cardiac monitoring system to form a twelve lead ECG signal for the complete heartbeat;

converting the twelve lead ECG signal of the complete heartbeat into a multi-dimensional representation of the complete heartbeat having orthogonal X, Y and Z lead data;

extracting a segment of the complete heartbeat from the orthogonal X, Y and Z lead data;

performing a principal component analysis on the extracted segment of the orthogonal X, Y and Z lead data to provide a synthesized signal that is most representative of the patient's electrical activity; and evaluating the orientation of a projection vector for the extracted segment defined by the synthesized signal.

8. The method of claim 7, wherein said extracting a segment includes extracting a T-wave segment, and wherein said evaluating the synthesized signal includes evaluating the shape of the T-wave segment defined by the synthesized signal.

9. The method of claim 7, wherein said extracting a segment includes extracting a T-wave segment.

10. The method of claim 9, wherein said evaluating the orientation of a projection vector includes evaluating the orientation of a projection vector with respect to a physical orientation of the patient.

11. The method of claim 7, wherein said extracting a segment includes extracting a T-wave segment and a QRS complex segment, and wherein said evaluating the synthesized signal includes evaluating the length of the QT interval as defined by the synthesized signal.

12. A system for evaluating an electrocardiogram (ECG) comprising:

a plurality of leads attachable to a patient, said plurality of leads configured to measure an electrical activity of a complete heartbeat of the patient; and a diagnostic system operatively connected to the plurality of leads, said diagnostic system configured to form a multi-lead signal for the complete heartbeat based on the measured electrical activity, convert the multi-lead signal into a multi-dimensional representation of the complete heartbeat having orthogonal X, Y and Z lead data, extract a segment of the orthogonal X, Y and Z lead data, transform the segment of the complete heartbeat from the orthogonal X, Y and Z lead data into a synthesized signal that most accurately reflects the patient's electrical activity, and evaluate the orientation of a projection vector for the extracted segment as defined by the synthesized signal.

13. The system of claim 12, wherein said plurality of leads include 10 leads.

14. The system of claim 12, wherein said multi-lead signal is a twelve lead signal.

* * * * *